United States Patent [19]
Yoon

[11] Patent Number: 5,797,939
[45] Date of Patent: Aug. 25, 1998

[54] ENDOSCOPIC SCISSORS WITH LONGITUDINAL OPERATING CHANNEL

[76] Inventor: InBae Yoon, 2101 Highland Ridge Dr., Phoenix, Md. 21131

[21] Appl. No.: 778,710

[22] Filed: Dec. 27, 1996

Related U.S. Application Data

[63] Continuation-in-part of Ser. No. 612,634, Mar. 4, 1996, and Ser. No. 376,186, Jan. 20, 1995, Pat. No. 5,665,100, which is a continuation-in-part of Ser. No. 281,814, Jul. 28, 1994, abandoned, which is a continuation of Ser. No. 73,193, Jun. 8, 1993, Pat. No. 5,334,209, which is a continuation of Ser. No. 720,381, Jun. 25, 1991, Pat. No. 5,217,473, which is a division of Ser. No. 446,555, Dec. 5, 1989, Pat. No. 5,026,379, said Ser. No. 612,634, is a continuation of Ser. No. 281,814.

[51] Int. Cl.$^6$ .................................................. A61B 17/04
[52] U.S. Cl. ........................... 606/167; 606/170; 606/174
[58] Field of Search ................................. 606/139–148, 606/167, 170, 174

[56] References Cited

U.S. PATENT DOCUMENTS

| | | |
|---|---|---|
| 2,002,594 | 5/1935 | Wappler et al. . |
| 2,004,559 | 6/1935 | Wappler et al. . |
| 2,011,169 | 8/1935 | Wappler . |
| 2,028,635 | 1/1936 | Wappler . |
| 2,031,682 | 2/1936 | Wappler et al. . |
| 2,032,860 | 3/1936 | Wappler et al. . |
| 2,068,721 | 1/1937 | Wappler et al. . |
| 2,316,297 | 4/1943 | Southerland et al. . |
| 2,518,994 | 8/1950 | Miller . |
| 2,691,370 | 10/1954 | Wallace . |
| 3,827,277 | 8/1974 | Weston . |
| 3,856,016 | 12/1974 | Davis . |
| 3,870,048 | 3/1975 | Yoon . |
| 3,871,379 | 3/1975 | Clarke . |
| 3,911,923 | 10/1975 | Yoon . |
| 3,958,576 | 5/1976 | Komiya . |
| 3,967,625 | 7/1976 | Yoon . |
| 3,980,086 | 9/1976 | Kletschka et al. . |
| 3,989,049 | 11/1976 | Yoon . |
| 4,049,002 | 9/1977 | Kletschka et al. . |
| 4,085,743 | 4/1978 | Yoon . |
| 4,103,680 | 8/1978 | Yoon . |
| 4,174,715 | 11/1979 | Hasson . |
| 4,226,239 | 10/1980 | Polk et al. . |
| 4,249,533 | 2/1981 | Komiya . |
| 4,249,535 | 2/1981 | Komiya . |
| 4,257,420 | 3/1981 | Terayama . |
| 4,274,415 | 6/1981 | Kanamoto et al. . |

(List continued on next page.)

FOREIGN PATENT DOCUMENTS

2469912  11/1979  France .

*Primary Examiner*—Gary Jackson

[57] ABSTRACT

A multifunctional endoscopic scissors instrument for use in performing endoscopic procedures within an anatomical cavity includes a handle and an elongate tubular member having a proximal end coupled with the handle for being disposed externally of the anatomical cavity and a distal end for being disposed within the anatomical cavity and carrying a pair of opposed, relatively movable blades. The blades are operable by manipulation of the handle to cut tissue and other objects such as, for example, lengths of suture material. In addition, the elongate tubular member defines a channel permitting fluids and other instruments to be communicated at the operative site without the need of having to remove the endoscopic scissors instrument from the body.

11 Claims, 4 Drawing Sheets

U.S. PATENT DOCUMENTS

| | | |
|---|---|---|
| 4,374,523 | 2/1983 | Yoon . |
| 4,393,872 | 7/1983 | Reznik et al. . |
| 4,427,014 | 1/1984 | Bel et al. . |
| 4,471,766 | 9/1984 | Terayama . |
| 4,484,581 | 11/1984 | Martin et al. . |
| 4,493,319 | 1/1985 | Polk et al. . |
| 4,644,951 | 2/1987 | Bays . |
| 4,662,371 | 5/1987 | Whipple et al. . |
| 4,669,470 | 6/1987 | Brandfield . |
| 4,674,501 | 6/1987 | Greenberg . |
| 4,712,545 | 12/1987 | Honkanen . |
| 4,739,760 | 4/1988 | Chin et al. . |
| 4,777,950 | 10/1988 | Kees, Jr. . |
| 4,788,966 | 12/1988 | Yoon . |
| 4,860,746 | 8/1989 | Yoon . |
| 4,869,268 | 9/1989 | Yoon . |
| 4,935,027 | 6/1990 | Yoon . |
| 4,949,717 | 8/1990 | Shaw . |
| 4,961,743 | 10/1990 | Kees, Jr. et al. . |
| 4,985,030 | 1/1991 | Melzer et al. . |
| 4,990,152 | 2/1991 | Yoon . |
| 5,015,249 | 5/1991 | Nakao et al. . |
| 5,026,379 | 6/1991 | Yoon . |
| 5,049,153 | 9/1991 | Nakao et al. . |
| 5,099,827 | 3/1992 | Melzer et al. . |
| 5,100,418 | 3/1992 | Yoon et al. . |
| 5,147,356 | 9/1992 | Bhatta . |
| 5,147,357 | 9/1992 | Rose et al. . |
| 5,147,373 | 9/1992 | Ferzli .................................... 606/144 |
| 5,152,780 | 10/1992 | Honkanen et al. . |
| 5,156,608 | 10/1992 | Troidl et al. . |
| 5,156,609 | 10/1992 | Nakao et al. . |
| 5,170,800 | 12/1992 | Smith et al. . |
| 5,171,250 | 12/1992 | Yoon . |
| 5,171,258 | 12/1992 | Bales et al. . |
| 5,172,700 | 12/1992 | Bencini et al. . |
| 5,176,695 | 1/1993 | Dulebohn . |
| 5,176,700 | 1/1993 | Brown et al. . |
| 5,192,298 | 3/1993 | Smith et al. . |
| 5,196,023 | 3/1993 | Martin . |
| 5,203,785 | 4/1993 | Slater . |
| 5,211,655 | 5/1993 | Hasson . |
| 5,217,030 | 6/1993 | Yoon . |
| 5,217,460 | 6/1993 | Knoepfler . |
| 5,217,473 | 6/1993 | Yoon . |
| 5,219,354 | 6/1993 | Choudhury et al. . |
| 5,220,928 | 6/1993 | Oddsen et al. . |
| 5,222,961 | 6/1993 | Nakao et al. . |
| 5,222,962 | 6/1993 | Burkhart . |
| 5,222,976 | 6/1993 | Yoon . |
| 5,226,908 | 7/1993 | Yoon . |
| 5,300,087 | 4/1994 | Knoepfler . |
| 5,318,589 | 6/1994 | Lichtman . |
| 5,334,199 | 8/1994 | Yoon . |
| 5,334,209 | 8/1994 | Yoon . |
| 5,342,381 | 8/1994 | Tidemand . |
| 5,342,389 | 8/1994 | Haber et al. . |
| 5,342,390 | 8/1994 | Slater et al. . |
| 5,366,459 | 11/1994 | Yoon . |
| 5,620,459 | 4/1997 | Lichtman ................................ 606/205 |

ENDOSCOPIC SCISSORS WITH LONGITUDINAL OPERATING CHANNEL

CROSS-REFERENCE TO RELATED APPLICATIONS

This application is a continuation-in-part of applicant's patent application Ser. No. 08/612,634, filed Mar. 4, 1996, pending and Ser. No. 08/376,186, filed Jan. 20, 1995, now U.S. Pat. No. 5,665,100 which are a continuation and a continuation-in-part, respectively, of patent application Ser. No. 08/281,814, filed Jul. 28, 1994, now abandoned which is a continuation of patent application Ser. No. 08/073,193, filed Jun. 8, 1993, now U.S. Pat. No. 5,334,209, which is a continuation of patent application Ser. No. 07/720,381, filed Jun. 25, 1991, now U.S. Pat. No. 5,217,473, which is a division of patent application Ser. No. 07/446,555, filed Dec. 5, 1989, now U.S. Pat. No. 5,026,379, the disclosures of which are incorporated herein by reference.

BACKGROUND OF THE INVENTION

1. Field of the Invention:

The present invention relates generally to medical procedures and instruments and, more particularly, to an endoscopic scissors with one or more longitudinal operating channels.

2. Discussion of the Related Art:

Endoscopic and minimally invasive medical procedures, such as laparoscopy, have become widely accepted for surgery and diagnosis due to the associated advantages relating to reduced trauma and hospitalization time. The performance of an endoscopic procedure typically involves creation of one or more puncture sites through a wall of an anatomical cavity using a penetrating instrument including an obturator, such as a trocar, disposed within a portal sleeve. After the penetrating instrument has penetrated into the anatomical cavity, the obturator is withdrawn leaving the sleeve in place to form a portal in the cavity wall for the introduction of instruments such as endoscopes, ligating appliers, forceps, cauteries and the like into the anatomical cavity.

Endoscopic procedures commonly involve performing a number of individual acts or functions within the anatomical cavity including grasping, cutting, coagulating, irrigating, aspirating, puncturing, injecting, dissecting, cauterizing, ligating, suturing, illuminating, visualizing and/or collecting specimens for biopsy. However, most endoscopic instruments are designed to perform only one of the above functions, requiring several incisions for placement of multiple portal sleeves to accommodate a suitable number of endoscopic instruments for performing the required functions or necessitating frequent withdrawal and replacement of individual endoscopic instruments through a single incision. While it is generally desirable to minimize the number of incisions created for performing a particular endoscopic procedure, substitution of instruments through a single incision can be time consuming, depending on the efficiency of the medical facility and staff, increasing the period of anesthetization for the patient. Additionally, internal bleeding can develop during the substitution of instruments thereby obscuring the field of view and requiring time consuming clean-up procedures to be performed.

A disadvantage of endoscopic instruments having articulated jaws, in particular, is that the jaws are typically mounted on pivots at the distal end of relatively long shafts requiring complicated and space-consuming linkages for converting the user's proximal movements into motion of the jaws increasing the risk of fluid leaking through poorly sealed pivotal mounts.

SUMMARY OF THE INVENTION

Accordingly, it is a primary object of the present invention to overcome the above-mentioned disadvantages of the prior art by providing an endoscopic scissors instrument with a longitudinal passage or channel formed therethrough for introducing additional instruments and/or fluids at the operative site without the need of having to remove the endoscopic scissors from the body.

Some of the advantages of the present invention over the prior art are that the endoscopic instrument can perform multiple functions through a single incision thereby minimizing the number of incisions required to perform an endoscopic procedure, that the frequency of substitution of instruments through a single incision can be reduced, that visualization of tissue through an operating channel formed through the instrument permits cutting operations to be performed with greater precision, that conventional handle structures can be used to provide users with a familiar feel and to decrease adaptation time, that the instrument can be fabricated at low cost using simple mechanisms without complicated linkages, and that the instrument can be sterilized for reuse or disposable for single patient use as desired.

These and other objects, advantages and benefits are realized with the present invention as generally characterized in a multifunctional endoscopic scissors instrument for use in performing endoscopic procedures within an anatomical cavity including a handle, an elongate tubular member having a proximal end coupled with the handle for being disposed externally of the anatomical cavity and a distal end for being disposed within the anatomical cavity and carrying a pair of opposed, relatively movable blades, the elongate tubular member defining a channel permitting access to an operative site within the anatomical cavity from outside the body, and means operable by manipulation of the handle for moving the blades relative to one another to perform cutting operations.

Other objects and advantages of the present invention will become apparent from the following description of the preferred embodiments taken in conjunction with the accompanying drawings, wherein like parts in each of the several figures are identified by the same reference numerals or by reference numerals having the same last two digits.

DESCRIPTION OF THE PREFERRED EMBODIMENTS

The endoscopic scissors instrument of the present invention can be utilized in any type of anatomical cavity; and, accordingly, while the instrument is described hereinafter for use with a portal sleeve in endoscopic procedures, such as laparoscopy, the instrument can be used with catheters and other small or large diameter tubular or hollow, cylindrical members providing access to small cavities, such as veins and arteries as well as large cavities, such as the abdomen.

Figure 1:
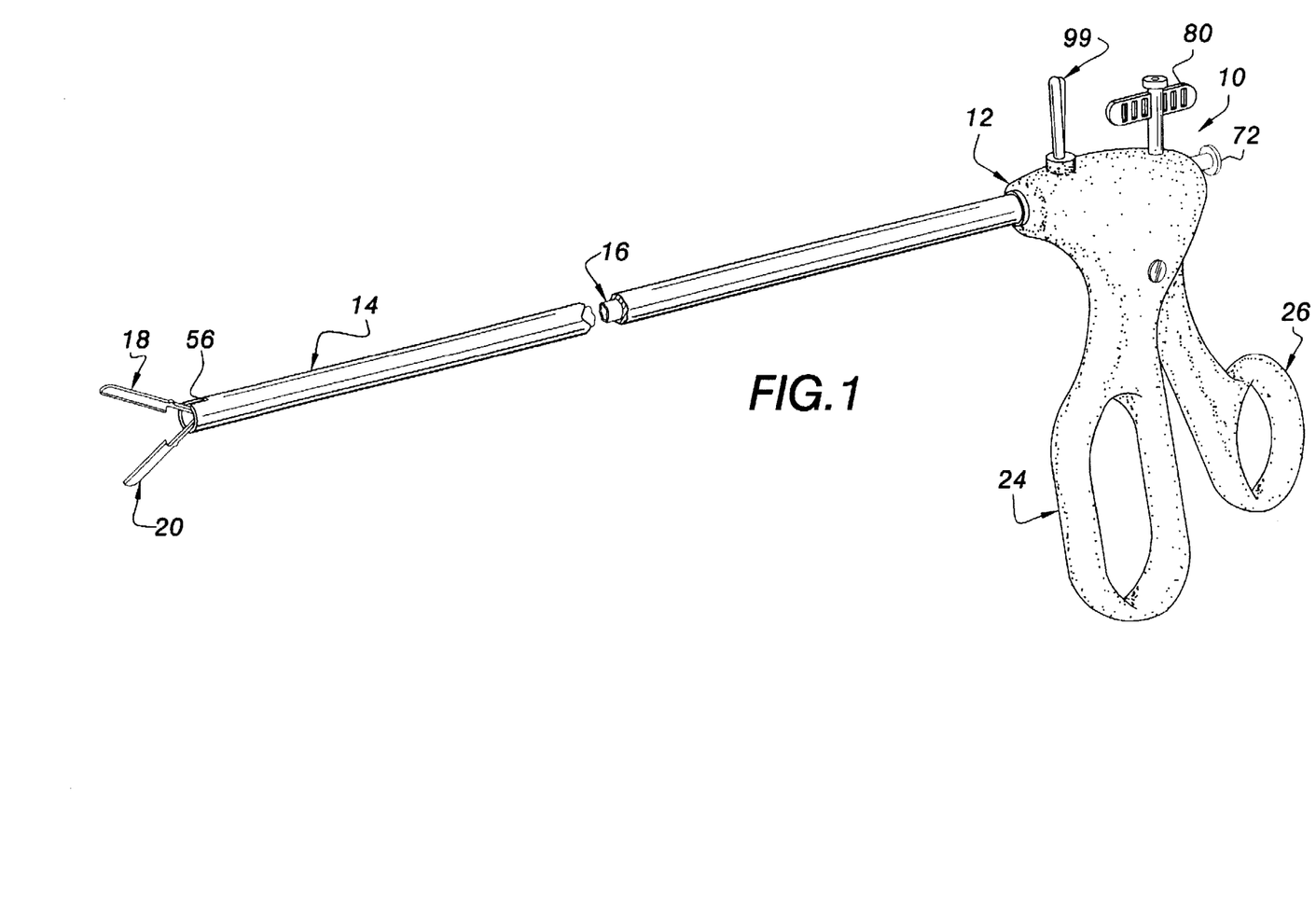
FIG. 1 is a perspective view, broken longitudinally, of an endoscopic scissors instrument according to the present invention.
Figure 2:
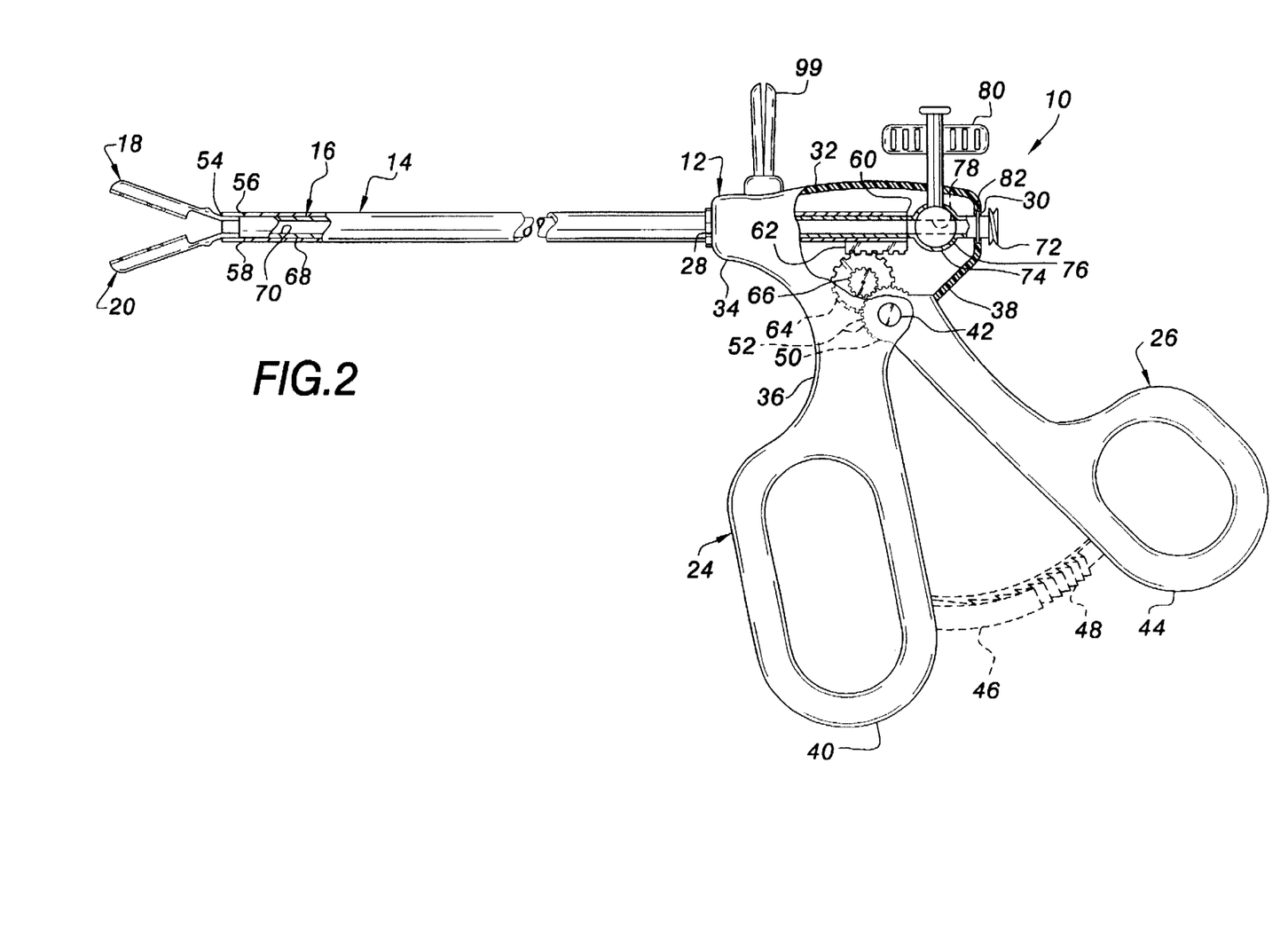
FIG. 2 is a broken side view, partly in section, of the endoscopic scissors instrument of FIG. 1 with the blades of the instrument in an open position.

An endoscopic scissors instrument 10 in accordance with the present invention, as illustrated in FIGS. 1 and 2, includes a housing 12, an outer tubular member 14 extending distally from the housing 12, an inner tubular member 16 telescopically fitted within the outer tubular member and terminating distally in a pair of opposed blades 18 and 20, and a handle portion formed of a fixed handle 24 and a movable handle 26.

Housing 12 includes longitudinally spaced front and rear walls 28 and 30 oriented perpendicular to a longitudinal axis of the instrument, a top wall 32 substantially parallel to the longitudinal axis and a bottom wall 34 having a concave forward portion 36 curving downwardly from the front wall to connect with an upper end of fixed handle 24 and a rearward portion 38 extending proximally at an angle relative to the longitudinal axis of the instrument from an upper end of the handle 24 to rear wall 30. A lower end of the fixed handle is configured as an elongate finger loop 40 to accommodate one or more fingers of a user. Movable handle 26 is pivotally mounted on a pin 42 proximally spaced from fixed handle 24 and secured internally to a wall or walls of the housing. A lower end of the handle 26 is configured as a finger loop 44 to accommodate one or more fingers of the user, and a pair of arcuate mating protrusions, shown by broken lines at 46 and 48 in FIG. 2, can optionally be carried in opposed relation on finger loops 40 and 44 for ratcheting engagement during operational use. Movable handle 26 includes an arcuate end portion 50 disposed within housing 12 and defining a plurality of gear teeth 52 on a side of pin 42 opposite finger loop 44.

Figure 3:
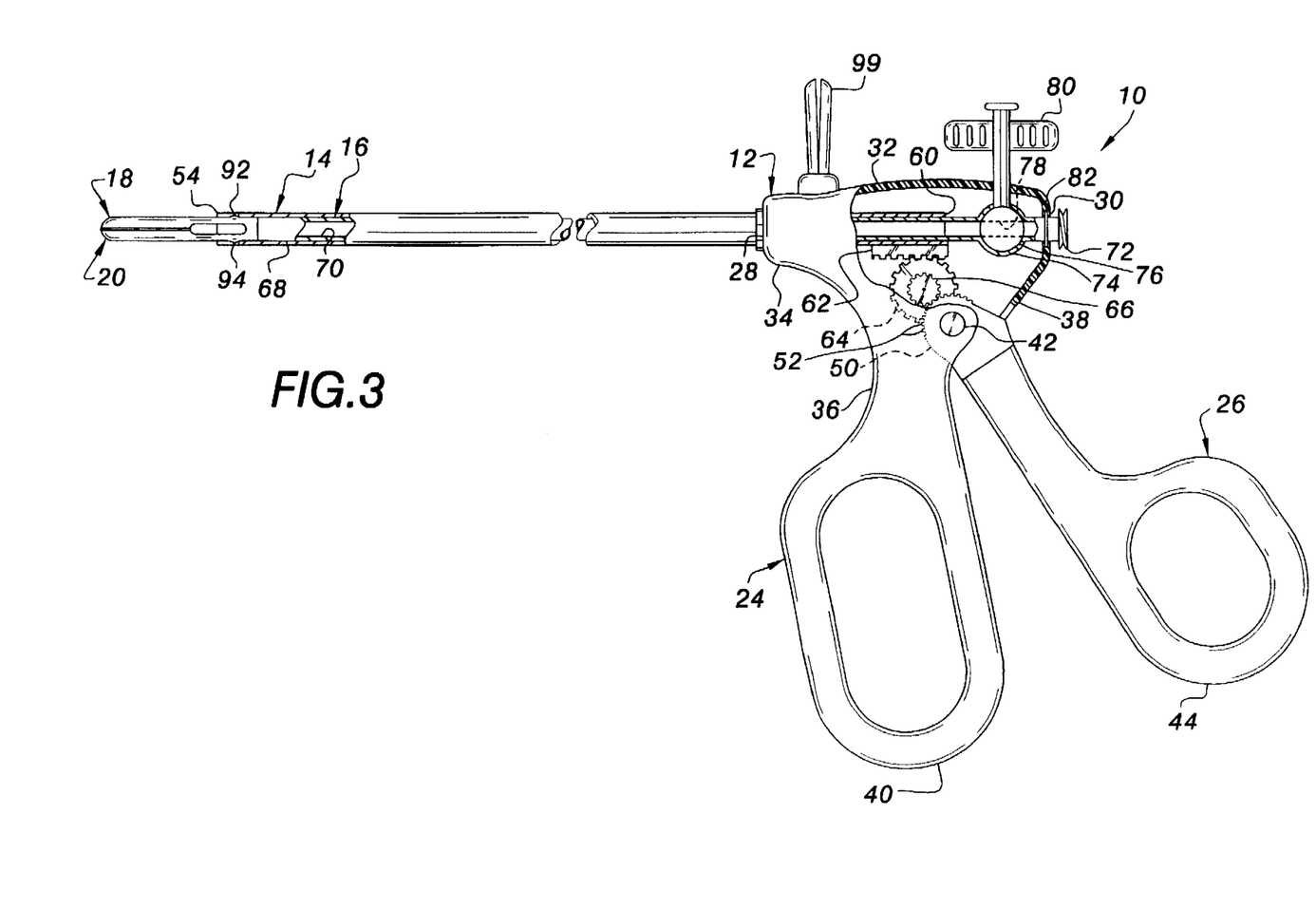
FIG. 3 is a broken side view, partly in section, of the endoscopic scissors instrument of FIG. 1 with the blades of the instrument in a closed position.
Figure 4:
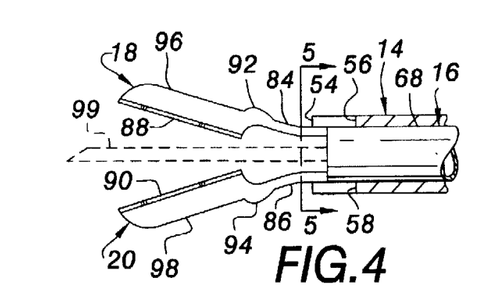
FIG. 4 is an enlarged fragmentary view of the distal end of the endoscopic scissors instrument of FIG. 1 with the blades of the instrument in the open position.

Outer tubular member 14 is open at both ends and extends distally from housing 12 through an opening in the front wall 28 of the housing. Preferably, the outer tubular member 14 is made of a cylindrical length of a substantially rigid material, such as stainless steel or some other medically acceptable metal or plastic material. Distal end 54 of the outer tubular member can be blunt as shown, tapered, beveled, or chamfered as desired or have any other suitable distal configuration; and, as best seen in FIG. 4, a pair of diametrically opposed longitudinal slots 56 and 58 preferably extend proximally from distal end 54 in circumferential alignment with blades 18 and 20, respectively. Proximal end 60 of the outer tubular member is movably disposed within the housing and carries a rack 62 in spaced relation to the toothed end portion 50 of handle 26. A pinion gear 64 engages the rack 62 and is mounted on the same shaft as a reduction gear 66 which meshingly engages toothed end portion 50 of the handle to convert relatively small rotary or pivotal movement of the handle into significantly larger linear movement of the rack. Looking at FIGS. 2 and 3, it will be appreciated that counterclockwise rotation of handle 26 about pin 42 results in proximal movement of outer tubular member 14 relative to housing 12 and that clockwise rotation of handle 26 about pin 42 results in distal movement of outer tubular member 14 relative to housing 12. In a preferred embodiment, movable handle 26 is biased in a clockwise direction toward fixed handle 24, for example by use of a torsion spring (not shown) coiled around pin 42 and connected between the movable handle and the fixed handle and/or the housing.

Figures 5, 7:
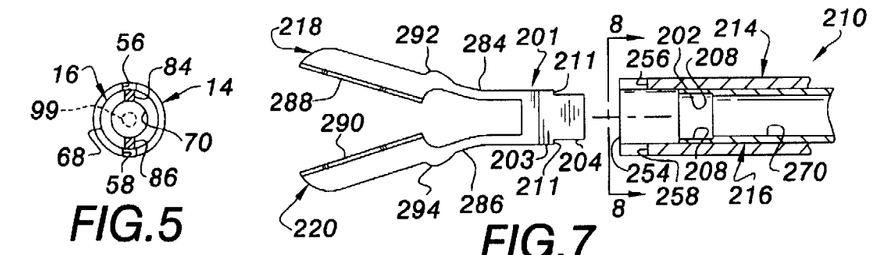
FIG. 5 is a cross-sectional view of the instrument blades taken through line 5—5 in FIG. 4.
FIG. 7 is an exploded fragmentary view of the distal end of another modification of the endoscopic scissors instrument according to the present invention.

Inner member 16 includes a tubular portion 68 telescopically fitted within outer tubular member 14 and defining a longitudinal lumen or channel 70 through the instrument. The proximal end of the inner member extends through the rear wall of housing 12 and terminates at a coupling 72, for example a Luer lock, for connection with sources of fluid or suction, other medical instruments and operating units such as those shown and described in my copending application Ser. No. 08/376,186, the disclosure of which has been incorporated herein by reference. A hollow, spherically-shaped valve housing 74 is distally spaced from the coupling within the housing, and a spherical valve member 76 having a cylindrical aperture or passage 78 formed therethrough is rotatably disposed within the valve housing and connected with a knob 80 extending upwardly through an opening in the top wall of the housing to permit manual operation of the valve from outside the housing. The inner member is fixed relative to the housing with a flange 82 mounted between the coupling and the valve and received within a slotted recess formed in rear wall 30. A pair of arms 84 and 86 extend distally from diametrically opposed locations on the distal end of tubular portion 68 and bend outwardly, away from the longitudinal axis of the tubular portion, to connect with integral one-piece blades 18 and 20, respectively, so that the blades are normally biased apart as shown in FIG. 2. Referring to FIGS. 4 and 5, in particular, blades 18 and 20 have an elongate, plate-like configuration with opposed inner edges 88 and 90 of the blades being sharp and laterally aligned or slightly offset to slidingly engage one another like a scissors when the blades are moved between the open position, state or condition shown in FIG. 2 and the closed position, state or condition shown in FIG. 3. While the blades are shown having a generally straight, planar configuration and an orientation substantially parallel to a longitudinal axis of the inner tubular member, it will be appreciated that the blades can be curved relative to the longitudinal axis in one or more planes and/or be oriented at any angle (e.g., 90°) relative to the longitudinal axis of the inner member dependent upon procedural use. Wedge-like cams 92 and 94 protrude outwardly from respective outer edges 96 and 98 of blades 18 and 20 and taper inwardly in the proximal direction to present an angled cam surface against which the distal end of outer tubular member 14 can act to force the blades together.

Tubular body 68 of the inner member is preferably formed with blades 18 and 20 as a single unitary part using a resilient medically-acceptable material such as, for example, a spring steel or a plastic material having suitable elastic properties for normally biasing the upper and lower blades apart while permitting the blades to be moved toward one another in response to forces acting on the outer edges of the blades and/or cams as a result of relative axial movement between the outer tubular member and the inner member. Alternatively, blades 18 and 20 can be formed separately of the tubular body and connected thereto in any suitable manner such as, for example, by adhesive bonding, welding or mechanical attachment. Preferably, the blades are formed of a medical grade metal material such as stainless steel or titanium.

An insulated connector 99 can optionally be mounted on housing 12 opposite the handle portion or at any other convenient location on the instrument to connect with electrically conductive elements of the instrument for performing unipolar or bipolar electric coagulation, for example using one or both of the blades as conductive elements.

In use, instrument 10 is grasped using finger loops 40 and 44 and is guided to the operative site via a portal sleeve positioned in the wall of an anatomical cavity. The portal sleeve can be positioned in the anatomical cavity wall using any suitable penetrating technique, including those creating puncture sites by means of removable obturators such as trocars, and can include a valve housing, if desired, to prevent loss of pneumoperitoneum during insertion and withdrawal of the instrument. Visualization of the endoscopic procedure can be accomplished using a conventional endoscope incorporated into the instrument, for example within the longitudinal channel 70 defined by tubular shaft 64, or separately positioned within the anatomical cavity through a second portal sleeve located at another puncture site.

Instrument 10 is advanced distally through the portal sleeve until blades 18 and 20 emerge into the anatomical cavity. At this point, the instrument can be manipulated externally of the body to position the blades at the operative site. Various cutting functions can be performed at the operative site by positioning objects such as anatomical tissue between the blades and by operating the handles of the instrument to open and close the blades as required. Since inner member 16 is fixed relative to housing 12, actuation of the blades to open or close is controlled by moving outer tubular member 14 relative to the inner member. If closed, blades 18 and 20 can be opened by moving outer tubular member 14 proximally relative to inner member 16. Movement of the outer tubular member over the inner member is controlled by operation of movable handle 26. Counterclockwise rotation of handle 26 about pin 42 results in clockwise rotation of reduction gear 66 which, in turn, causes an equal angular rotation of pinion 64. Pinion 64 is of greater diameter than reduction gear 66 so that, for equal angles of rotation, pinion 64 will produce greater circumferential displacement. Pinion 64 engages the gear teeth of rack 62 to cause proximal movement of the outer tubular member 14 relative to blades 18 and 20 thereby permitting the blades to move resiliently to the open position shown in FIG. 2. In the open position, blades 18 and 20 are biased apart such that cutting edges 88 and 90 of the blades are angularly spaced from one another allowing objects to be positioned between the blades. Conversely, clockwise rotation of the handle 26 about pin 42 results in counterclockwise rotation of reduction gear 66 and pinion 64 causing distal movement of rack 62 and outer tubular member 14 relative to the blades so that distal end 54 of the outer tubular member will slide over the blades in an axial direction causing respective outer edges and/or cams of the blades to be received in slots 56 and 58, as shown in FIG. 3, thereby camming the blades inwardly from the open position to the closed position while at the same time stabilizing the blades to prevent misalignment and splaying. As the blades move from the open position to the closed position, cutting edges 88 and 90 of the blades will slidingly engage one another like a scissors to cut objects, such as tissue or unsecured lengths of suture material, placed between the blades when the blades are in the open position.

Movable handle 26 is preferably proximally spaced from fixed handle 24 as shown so that the user can maintain one or more fingers on the stationary handle 24 while operating the movable handle 26 with the thumb and/or other fingers of the hand. Movable handle 26 is preferably biased in a clockwise direction, looking at FIG. 3, toward stationary handle 24 so that, when the movable handle is released, outer tubular member 14 will be automatically moved over blades 18 and 20 to close the blades together, for example to protect organs and other structures of the body from damage during complicated maneuvers requiring free hand movement.

In addition to performing various cutting functions, the endoscopic scissors instrument 10 permits access to the operative site from outside the body through channel 70 formed through the instrument between proximal and distal ends of the inner tubular member. The channel can, for example, be used to introduce lengths of suture material (with or without knotting elements attached thereto) as well as any other medical devices or instruments, such as endoscopes or probes, or to perform irrigation or aspiration at the operative site, for example by attaching a source of fluid or suction to the coupling at the proximal end of the inner member, or to administer medicaments as desired. In FIGS. 4 and 5, for example, a tubular needle 99 is shown protruding distally from channel 70 to penetrate tissue and/or administer medicaments to the operative site.

Figure 6:
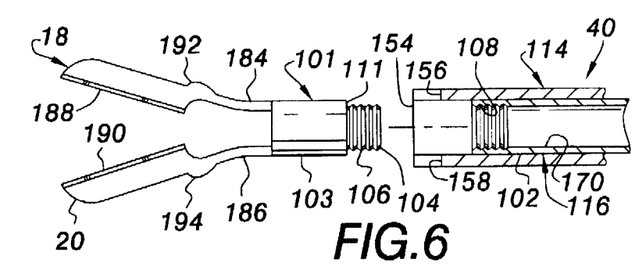
FIG. 6 is an exploded fragmentary view of the distal end of a modification of the endoscopic scissors instrument according to the present invention.

The instrument blades can be integrally formed with the inner tubular member as shown or they can be formed separately of the inner tubular member and detachably coupled therewith to facilitate sterilization or to permit replacement. For example, in FIG. 6, a modification of the endoscopic scissors instrument according to the present invention is shown wherein the blades 118 and 120 of the modified instrument 110 are mounted on a coupling 101 having a hollow cylindrical body 103 with a proximal portion 104 configured to mate with a cooperatively configured distal portion 102 of the inner tubular member 116. Arms 184 and 186 extend distally from diametrically opposed locations at the distal end of cylindrical body 103 to connect with blades 118 and 120 and bend outwardly as described above to bias the blades apart. Cylindrical body 103 has an outer diameter approximately equal to the outer diameter of inner tubular member 116 to fit telescopically within outer tubular member 114. The cylindrical body terminates proximally at a radial step or shoulder 111 connecting the cylindrical body with proximal portion 104 of the coupling, the proximal portion being of somewhat smaller diameter and provided with external threads 106 to couple with internal threads 108 on distal portion 102 of the inner tubular member.

Figure 8:
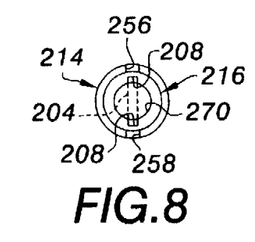
FIG. 8 is a front view of the blade mounting portion of the endoscopic scissors instrument of FIG. 7.

FIGS. 7 and 8 illustrate another modification of the endoscopic scissors instrument according to the present invention wherein the blades 218 and 220 of the modified instrument 210 are mounted on a coupling 201 having a generally rectangular plate-like body 203 with a proximal portion 204 configured to mate with a cooperatively configured distal portion 202 of the inner tubular member 216. Arms 284 and 286 extend distally from opposite lateral edges at the distal end of body 203 to connect with blades 218 and 220 and bend outwardly as described above to bias the blades apart. Rectangular body 203 has a lateral dimension or width approximately equal to the outer diameter of inner tubular member 216 to fit diametrically within outer tubular member 214. The rectangular body terminates proximally at a pair of inwardly extending notches, steps or shoulders 211 formed along opposite lateral edges of the body and connecting the rectangular body with proximal portion 204 of the coupling, the proximal portion being of generally rectangular configuration but with somewhat smaller width to fit frictionally within diametrically opposed slots 208 formed along an inner surface of distal portion 202. In the assembled condition, shown by broken lines in FIG. 8, the coupling divides channel 270 into a pair of apertures, either or both of which may be used to position instruments alongside the blades at laterally offset positions not interfering with operation of the blades.

Figure 9:
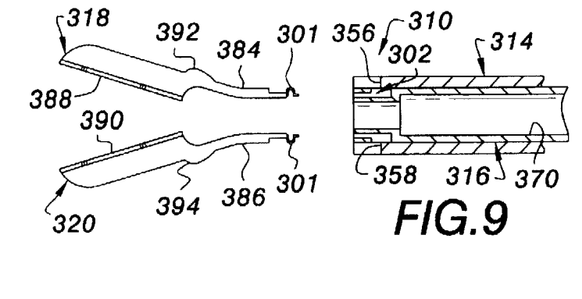
FIG. 9 is an exploded fragmentary view of the distal end of yet another modification of the endoscopic scissors instrument according to the present invention.
Figure 10:
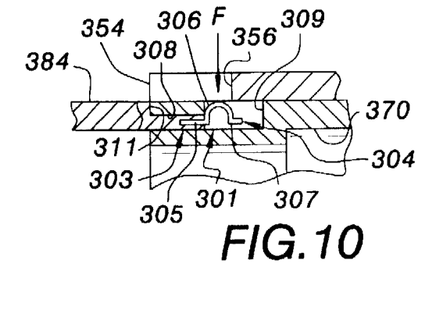
FIG. 10 is an enlarged fragmentary view of the blade mounting portion of the endoscopic scissors instrument of FIG. 9.

In yet another modification of the endoscopic scissors instrument according to the present invention, shown in FIGS. 9 and 10 at 310, each of the blades 318 and 320 carries a separate coupling 301 having an elongate, finger-like member or body 303 extending proximally from a step or shoulder 311 at a proximal end of each arm to a proximal portion 304 in the form of a resilient detent. Detent 304 is formed of a strip or band of a resilient material, such as spring steel, and includes a longitudinal portion 305 extending proximally from body 303 to an outwardly curved convex portion 306 which extends laterally outward from the longitudinal portion to an apex where it bends back inwardly to connect with a longitudinal extension 307 having a free end. The detent is configured to mate cooperatively with a distal portion 302 of the inner tubular member 316 which includes a longitudinal passage 308 extending proximally from a distal end of the inner tubular member to a transverse opening 309 in the side of the inner tubular member.

The blades 318 and 320 are assembled with the inner tubular member by inserting proximal portion 301 of the blade coupling into the openings formed in distal portion 302 of the inner tubular member. Detent 304 is resiliently deformed or compressed in longitudinal passage 308 during insertion but will expand laterally outward into opening 309 upon emerging from the passage. At about the same time, shoulder 311 is caused to abut the distal end of the inner tubular member so that the blade is fixed in place and prevented from moving. To remove the blades, convexly curved portion 306 of the detent is pressed inwardly in the direction of the arrow in FIG. 10 to compress the curved portion so it can slide within the passage as the blade is pulled in a distal direction relative to the inner tubular member.

From the above, it will be appreciated that the endoscopic scissors instrument according to the present invention permits anatomical tissue and other objects to be cut at an operative site while defining a channel for fluids and other medical instruments, devices and probes to be introduced at the operative site without the need of having to remove the endoscopic scissors from the body.

The blades can each be formed as an integral one-piece unit or assembled from separate pieces; and, depending on procedural use, one of the blades can be fixed and the other movable, both blades can be movable, the blades can be linked by pivots or formed at the end of a tubular member or formed at the end of a pair of pivotally connected arms. The blades can be straight, curved and/or angled as desired. Any of the blades shown or described herein can be formed with straight, serrated or combined cutting edges.

The blades can be centrally located for cutting anatomical tissue, unsecured lengths of suture material or any other objects normally cut during a surgical procedure, or the blades can be offset laterally from the central longitudinal axis of the endoscopic portion of the instrument to permit better visualization. The blades can be laterally offset from one another in a manner to permit sliding contact with scissor-like cutting, or the blades can be substantially laterally aligned to permit direct abutment of cutting edges to produce a chopping cut.

The handle portion of the endoscopic scissors instrument shown and described herein is exemplary of the types of conventional handle mechanisms suitable for performing the function of actuating the blades; accordingly, the handles can have any configuration to actuate the blades including, but not limited to, configurations employing a pair of pivotally connected arms, one fixed and one pivoted arm, a pistol grip with a movable trigger, or resilient U-shaped handle members. Further, the handle portion of the instrument can be configured to rotate relative to a pivot axis oriented perpendicular to the longitudinal axis of the instrument so that, for example, in one position the handles will extend laterally from the instrument or at a substantially perpendicular angle relative to the longitudinal axis; while, in another position, the handles will extend proximally from the instrument like scissor handles.

It will be appreciated that the handle portion and blade portion of the endoscopic scissors instrument can be integrally formed as a one-piece unit or formed as separate components and coupled together, for example, by use of pivots, linkages, rods, cables, telescoping members, brackets and other mechanical and/or electrical couplings.

When the instrument is formed of telescoping members, it will also be appreciated that individual telescoping members, such as the inner member, can be made rotatable about a longitudinal axis of the instrument either alone or in combination with other telescoping members. Moreover, when the instrument is coupled with a source of fluid or suction, an operating unit or other medical device, the instrument housing can have any configuration for being releasably coupled including, but not limited to threaded or telescoping portions, detents, latches or any other suitable connections. Furthermore, the housing can be cylindrical or rectangular or have any other useful or convenient shape or cross-sectional configuration.

The inner member is preferably of hollow cylindrical configuration but can have any elongate tubular configuration defining one longitudinal channel as shown or multiple longitudinal channels of similar or different cross-sectional configuration. Any of the channels defined by the inner member can be coaxially disposed or laterally offset from the central longitudinal axis of the inner member and can have any suitable configuration in cross-section dependent upon procedural use including, but not limited to, circular, elliptical and polygonal cross-sectional configurations. Furthermore, the outer surface of the inner tubular member can be of circular of cylindrical cross-sectional configuration as shown or have any other external shape in cross-section including, but not limited to, elliptical and polygonal cross-sectional configurations.

The outer tubular member can have any suitable configuration in cross-section to fit through a portal formed in the wall of an anatomical cavity and to receive the inner member for sliding movement therein. The distal end of the outer tubular member can be blunt, tapered, beveled or chamfered, and can also be provided with interior grooves or slots for receiving protrusions or cams carried on the outer surfaces of the blades to assist in maintaining proper alignment of the blade blades when cutting tough materials. Alternatively, protrusions can be carried on an interior surface of the outer tubular member in alignment with slots or grooves formed in the blades to maintain alignment during operational use.

The components of the endoscopic scissors instrument of the present invention can be made of any suitable, medical grade materials to permit sterilization for reuse or disposal for single patient use. The components can be made of multiple parts of various configurations and materials to reduce cost and/or simplify fabrication. The instrument can have various valves, stop cocks and seals in the housing and/or inner member to control fluid flow therethrough. In addition, one or both blades can be used to transmit energy at the operative site such as, for example, electrical, ultrasound or thermal energy.

The features of the various embodiments described above can be combined in any manner desired dependent upon the operational requirements of the procedure to be performed and the complexity of the endoscopic scissors instrument.

Inasmuch as the present invention is subject to many variations, modifications and changes to detail it is intended that all subject matter discussed above or shown in the accompanying drawings be interpreted as illustrative only and not be taken in a limiting sense.

What is claimed is:

1. A multifunctional endoscopic scissors instrument for use in performing endoscopic procedures within an anatomical cavity comprising a handle;

an elongate tubular member having a proximal end coupled with said handle for being disposed externally of the anatomical cavity and a distal end for being disposed within the anatomical cavity and carrying a pair of opposed, relatively movable blades, said elongate tubular member defining a channel permitting access to an operative site within the anatomical cavity from outside the body;

said blades being movable relative to one another by manipulation of said handle to perform cutting operations.

2. A multifunctional endoscopic scissors instrument for use in performing endoscopic procedures within an anatomical cavity as recited in claim 1 wherein said blades are biased apart toward an open position and further comprising an outer tubular member disposed telescopically around said elongate tubular member and having a proximal end coupled with said handle and a distal end movable relative to said elongate tubular member by manipulation of said handle between a retracted position allowing said blades to open and an extended position causing said blades to close.

3. A multifunctional endoscopic scissors instrument for use in performing endoscopic procedures within an anatomical cavity as recited in claim 2 wherein at least one slot is formed at a distal end of said tubular outer member in circumferential alignment with one of said blades to receive and stabilize said blade during cutting operations.

4. A multifunctional endoscopic scissors instrument for use in performing endoscopic procedures within an anatomical cavity as recited in claim 2 wherein a pair of slots are formed at a distal end of said tubular outer member in circumferential alignment with said blades to receive and stabilize said blades during cutting operations.

5. A multifunctional endoscopic scissors instrument for use in performing endoscopic procedures within an anatomical cavity as recited in claim 1 and further comprising a coupling detachably coupled with said elongate tubular member for mounting said opposed, relatively movable blades.

6. A multifunctional endoscopic scissors instrument for use in performing endoscopic procedures within an anatomical cavity as recited in claim 5 wherein said coupling includes a cylindrical body having a proximal portion configured to threadedly engage a distal portion of said elongate tubular member.

7. A multifunctional endoscopic scissors instrument for use in performing endoscopic procedures within an anatomical cavity as recited in claim 5 wherein said coupling includes a body having a proximal portion configured to frictionally engage a distal portion of said elongate tubular member.

8. A multifunctional endoscopic scissors instrument for use in performing endoscopic procedures within an anatomical cavity as recited in claim 6 wherein a pair of diametrically opposed grooves are formed along an inner surface of said distal portion of said elongate tubular member and said coupling includes a plate-like member configured to slide along said grooves.

9. A multifunctional endoscopic scissors instrument for use in performing endoscopic procedures within an anatomical cavity as recited in claim 5 wherein said elongate tubular member includes a recess and said coupling includes a mechanical detent configured to be received within said recess.

10. A multifunctional endoscopic scissors instrument for use in performing endoscopic procedures within an anatomical cavity as recited in claim 1 and further comprising at least one flexible arm connecting one of said blades with said distal end of said elongate tubular member.

11. A multifunctional endoscopic scissors instrument for use in performing endoscopic procedures within an anatomical cavity as recited in claim 1 wherein at least one of said blades is electrically conductive and further comprising an insulated connector coupled with said electrically conductive blade for connecting a cauterizing current to said blade.

* * * * *